US005637298A

United States Patent [19]
Stowell

[11] Patent Number: 5,637,298
[45] Date of Patent: Jun. 10, 1997

[54] COMPOSITION AND METHOD FOR KILLING TERMITES

[75] Inventor: John C. Stowell, New Orleans, La.

[73] Assignee: Board of Supervisors of Louisiana State University and Agricultural and Mechanical College, Baton Rouge, La.

[21] Appl. No.: 664,337

[22] Filed: Jun. 14, 1996

[51] Int. Cl.⁶ .......................... A01N 25/00; A01N 43/40; A01N 47/28; A01N 55/00

[52] U.S. Cl. ............................ 424/84; 424/659; 424/660; 514/63; 514/341; 514/345; 514/594; 514/601

[58] Field of Search ............................ 424/84, 659, 660; 514/63, 341, 345, 594, 601

[56] References Cited

U.S. PATENT DOCUMENTS 5,177,107  1/1993  Meer et al. ............................ 514/553

OTHER PUBLICATIONS

G. Prestwich et al., "Structure–Activity Relationships among Aromatic Analogs of Trail–Following Pheromone of Subterranean Termites," *J. Chem. Ecology*, vol. 10, pp. 1201–1217 (1984).

Declaration of Gregg Henderson (Jun. 14, 1996).

*Primary Examiner*—Allen J. Robinson
*Attorney, Agent, or Firm*—John H. Runnels

[57] ABSTRACT

2-naphthalenemethanol [Chemical Abstracts registry no. 1592-38-7] produces a high degree of trail-following activity in termites. The attractant 2-naphthalenemethanol and certain derivatives increase bait acceptance by termites, improving the ability of termite baits to kill colonies, allowing lower amounts of toxicant to be used, or both.

12 Claims, No Drawings

COMPOSITION AND METHOD FOR KILLING TERMITES

The development of this invention was partially funded by the Government under grant CR 818568-01 awarded by the Environmental Protection Agency. The Government may have certain rights in this invention.

This invention pertains to an attractant and bait additive for termites.

The Formosan subterranean termite, *Coptotermes formosanus* Shiraki, is a major worldwide pest that attacks both living trees and structural wood. Unlike other subterranean termites, the Formosan termite can establish a colony that does not touch the ground.

*Coptotermes formosanus* is native to southeast Asia, but is now also found in Hawaii, along the southeastern Atlantic coast of the United States, and in the Gulf South of the United States, Guam, Midway Island, Brazil, Sri Lanka, and Africa. First discovered in the United States by pest control operators in 1965, *C. formosanus* has gradually expanded its geographic domain. The largest single locus of *C. formosanus* in the United States is in south Louisiana, with heavy infestations in Lake Charles and New Orleans.

*C. formosanus* continues to cause great structural damage to many buildings in the Lake Charles and New Orleans areas, including damage to many buildings of historic significance. There is particular concern for the future of New Orleans' French Quarter, where many historic buildings are already severely damaged and would be quite expensive to repair.

Three principal methods have been used in the past to control Coptotermes: (1) chemical and physical barriers to prevent termites from attacking wood, (2) wood preservatives and termiticides used to protect infested or susceptible wood, and (3) destruction of a termite colony by excavation of the nest.

Chemical barriers and termiticides have generated public concern over environmental safety.

In China excavation of the nest has been one of the main methods used to control Formosan termites. However, locating a termite nest is typically very time-consuming, limiting the usefulness of the practice.

Using a bait to deliver a termiticide has several advantages. Baits typically require only a small amount of the toxicant, and they target only the insects that feed on the bait. Thus non-target organisms are not affected, diminishing the environmental impact of the use of toxicants. Use of a bait often makes it unnecessary to locate the nest, because many termites, including Formosan termites, engage in trophallaxis (transfer of food to other colony members). Thus the toxicant may be spread throughout a colony after feeding by only a few foraging termites. Bait methods have previously been used to detect and experimentally control subterranean termites, and to trap termites for studies on termite ecology.

A major problem with existing baiting techniques against Coptotermes species has been inconsistent bait acceptance. Baits placed within termite galleries are often bypassed and left uneaten. The use of termite baits is different from the use of ant baits and cockroach baits, because it is usually not possible to remove competing food sources for termites. Attractants and food stimulants can sometimes increase the consistency of bait acceptance, but there remains a continuing need for improved termite baits.

G. Prestwich et al., "Structure-Activity Relationships among Aromatic Analogs of Trail-Following Pheromone of Subterranean Termites," *J. Chem. Ecology*, vol. 10, pp. 1201–1217 (1984) discloses that (Z)-4-phenyl-3-buten-1-ol ("PBO") produced trail-following activity in five species in four genera of termites. PBO was more active than any of 12 other PBO analogs tested. A proposed schematic drawing of the receptor site of a putative (and unidentified) pheromone receptor was given.

It has been unexpectedly discovered that 2-naphthalenemethanol [Chemical Abstracts registry no. 1592-38-7] produces a high degree of trail-following activity in termites. The attractant 2-naphthalenemethanol increases bait acceptance by termites, improving the ability of termite baits to kill colonies, allowing lower amounts of toxicant to be used, or both. The attractant 2-naphthalenemethanol is less expensive than PBO. Certain derivatives of 2-naphthalenemethanol have similar activity.

The response of soldiers to PBO appears to be the reverse of the response of workers—at higher concentrations, more workers follow a PBO trail, but fewer soldiers. By contrast, the response of both workers and soldiers to 2-naphthalenemethanol is similar—higher concentrations cause greater numbers of both soldiers and workers to follow a trail. The positive response by both workers and soldiers is a distinct advantage when one wishes termites to consume a bait containing a toxicant; the presence of both castes increases a colony's overall consumption of the bait.

Formosan termites were collected from a colony in New Orleans, Louisiana. Collected termites were maintained in plastic containers (20 cm diameter, 20 cm high), that were kept at room temperature, and that contained moistened soil, cardboard, and wood. Termites were extracted from the colony with cardboard baits for use in the experiments described below.

Three compounds were evaluated at four different concentrations each for their ability to cause trail-following behavior in *C. formosanus*. The three compounds tested were PBO (93% Z isomer, 7% E isomer), 2-naphthalenemethanol, and 3-phenoxy-1-propanol. The trail-following assay was modified from that of G. Prestwich et al., "Structure-Activity Relationships among Aromatic Analogs of Trail-Following Pheromone of Subterranean Termites," *J. Chem. Ecology*, vol. 10, pp. 1201–1217 (1984). One day before the assay, workers were isolated from the colony, and kept on a piece of cardboard in a Petri dish to minimize feeding and colony odor contamination. Two workers were kept in each Petri dish. Five microliters of each test solution in 95% ethanol were applied to a 10-cm semicircular pencil trail on Consolith™ paper. One termite was tested on each paper. Twenty replicates were conducted for each concentration for each termite caste. One termite was placed at one end of the trail on the paper strip, and its behavior was monitored continuously for a maximum of five minutes. A positive score was recorded if the termite followed half or more of a trail.

The best results were obtained with 2.5 mg/mL 2-naphthalenemethanol. Tables 1–3 show the average number of positive scores for each compound at each concentration.

TABLE 1

Z-4-Phenyl-3-buten-1-ol

| Concentration (mL/L) | Workers | Soldiers |
|---|---|---|
| 0.78 | 16 | 3 |
| 0.39 | 12 | 7 |
| 0.18 | 11 | 5 |
| 0.09 | 6 | 8 |

For the Z-4-phenyl-3-buten-1-ol, the workers showed a significant dose response at the concentrations tested, while the soldiers did not. There was a significant difference between the response of the workers and the response of the soldiers.

TABLE 2

3-Phenoxy-1-propanol

| Concentration (mL/L) | Workers | Soldiers |
| --- | --- | --- |
| 100 | 14 | 10 |
| 50 | 12 | 7 |
| 25 | 10 | 5 |
| 12.5 | 7 | 3 |

For the 3-phenoxy-1-propanol, although trends were apparent in the dose response for both workers and soldiers, neither of these trends was statistically significant at the P=0.05 level. There was not a significant difference between the response of the workers and the response of the soldiers.

TABLE 3

2-Naphthalenemethanol

| Concentration (mg/mL) | Workers | Soldiers |
| --- | --- | --- |
| 2.5 | 19 | 12 |
| 1.25 | 13 | 11 |
| 1.0 | 9 | 8 |
| 0.63 | 4 | 4 |

For the 2-naphthalenemethanol, the workers and soldiers both showed a significant dose response at the concentrations tested. There was not a significant difference between the response of the workers and the response of the soldiers. Both responded positively to increasing concentrations of 2-naphthalenemethanol.

The attractant 2-naphthalenemethanol may be substituted at the 7 or 8 position of the naphthalene ring structure, so long as the substituent is not so bulky that it will sterically hinder binding in the receptor site. Such compounds have the generic designation 2-hydroxymethyl-7-$R^1$-8-$R^2$-naphthalene. $R^1$, for example, may be methyl, ethyl, propyl, or isopropyl; $R^2$, for example, may be methyl, ethyl, propyl, or isopropyl.

In a preferred embodiment of this invention, an effective amount of an attractant in accordance with this invention is mixed with a toxicant for termites, preferably by impregnating both into a termite bait such as cardboard. When the impregnated bait is placed in the vicinity of a termite colony, termites will preferentially feed on the treated bait, thereby consuming the toxicant, and typically thereafter introducing the toxicant to other members of the colony as well. As used in the specification and in the claims below, an "effective amount" of an attractant is an amount that, when mixed with a termite toxicant in a bait, will increase the rate of consumption of the toxicant by termites to at least ten percent above the rate of consumption of an otherwise comparable bait lacking the attractant.

In another preferred embodiment, the attractant need not necessarily be incorporated into a bait containing a toxicant. The attractant may be used to lead termites to the bait. For example, the attractant may be mixed with a surfactant, and the mixture placed on or near the bait. Applying water to the surfactant/attractant mixture causes the attractant to form trails with gradients leading to the bait. In other contexts, termites are known to follow gradients of attractants. Thus the trails lead the termites to the bait, which they then consume and distribute to other members of the colony.

The toxicant used in this invention may be any substance that kills termites or impedes their growth, including chemical insecticides; pathogenic nematodes, fungi, protozoans, or bacteria; or biological controls such as insect growth regulators. Preferred toxicants are slow-acting (i.e., acting over a course of hours, days, or weeks, preferably days or weeks), to reduce "avoidance" effects before individuals have distributed food to other members of the colony. Several suitable slow-acting toxicants for termites are known in the art, and include, for example silafluofen; borates (boric acid, disodium octaborate tetrahydrate); sulfluramid and other fluoroalkyl sulfonamides; avermectin; hydramethylnon; hexaflumuron and other chitin synthesis inhibitors and other acyl ureas; diflubenzuron (Dimilin); azadirachtin; dechlorane (Mirex); diiodomethyl-para-tolyl sulfone (A-9248); fluorosulfonates; imidacloprid; azadirachtin; cyromazine; juvenile hormones and juvenile hormone mimics or analogs such as fenoxycarb, methoprene, hydroprene, triprene, furnesinic acid ethyl and alkoxy derivatives, and pyriproxyfen (Nylar); and the plant *Rheuneo jupanic* Thunb. Roth. In addition, otherwise faster-acting insecticides may act more slowly if microencapsulated. Biological control agents that may be used as toxicants include fungi that are pathogenic to insects, such as *Metarhizium anisopliae*, *Aspergillus flavus*, and *Beauveria bassiania*; nematodes that are pathogenic to insects, such as *Neoplectana carpocapsae*; insect viruses; pathogenic bacteria such as *Bacillus thuringiensis* and *Serratia marcescens*; or toxins derived from biological control agents such as *Bacillus thuringiensis* toxin.

Preferred termite bait materials include cardboard, paper, and dried semi-aqueous cellulose mixtures. An alternative to impregnation of the bait is to manufacture paper or cardboard containing the toxicant and attractant in the paper or cardboard from the beginning. Adding moisture to the bait can help increase its attractiveness to termites.

The toxicant and attractant may be administered via a bait station, such as that disclosed in commonly-assigned United States patent application Ser. No. 08/568,811, filed Dec. 7, 1995 now pending.

The entire disclosures of all references cited in this specification are hereby incorporated by reference in their entirety. In the event of an otherwise irresolvable conflict, however, the present specification shall control.

I claim:

1. A composition of matter for killing termites, comprising a termite toxicant and an effective amount of 2-naphthalenemethanol; wherein an effective amount of said 2-naphthalenemethanol is an amount that will increase the rate of consumption of said toxicant by termites to at least ten percent above the rate of consumption of an otherwise comparable composition of matter lacking said 2-naphthalenemethanol.

2. A method for killing termites, comprising the steps of placing near a termite colony a termite bait, and allowing the termites to consume a sufficient amount of the bait to kill at least some of the termites in the colony; wherein said termite bait comprises a termite toxicant and an effective amount of 2-naphthalenemethanol; wherein an effective amount of said 2-naphthalenemethanol is an amount that will increase the rate of consumption of said toxicant by termites to at least ten percent above the rate of consumption of an otherwise comparable termite bait lacking said 2-naphthalenemethanol.

3. A method as recited in claim 2, wherein the termites are *Coptotermes formosanus*.

4. A method for killing termites, comprising the steps of placing near a termite colony a termite bait containing a termite toxicant; creating at least one trail of 2-naphthalenemethanol to lead termites to the bait; and allowing the termites to consume a sufficient amount of the bait to kill at least some of the termites in the colony.

5. A method as recited in claim 4, wherein the termites are *Coptotermes formosanus*.

6. A composition of matter for killing termites, comprising a termite toxicant and an effective amount of a termite attractant comprising 2-hydroxymethyl-7-$R^1$-8-$R^2$-naphthalene; wherein $R^1$ is methyl, ethyl, propyl, or isopropyl; wherein $R^2$ is methyl, ethyl, propyl, or isopropyl; and wherein an effective amount of said termite attractant is an amount that will increase the rate of consumption of said toxicant by termites to at least ten percent above the rate of consumption of an otherwise comparable composition of matter lacking said termite attractant.

7. A method for killing termites, comprising the steps of placing near a termite colony a termite bait, and allowing the termites to consume a sufficient amount of the bait to kill at least some of the termites in the colony; wherein said termite bait comprises a termite toxicant and an effective amount of a termite attractant comprising 2-hydroxymethyl-7-$R^1$-8-$R^2$-naphthalene; wherein $R^1$ is methyl, ethyl, propyl, or isopropyl; wherein $R^2$ is methyl, ethyl, propyl, or isopropyl; and wherein an effective amount of said termite attractant is an amount that will increase the rate of consumption of said toxicant by termites to at least ten percent above the rate of consumption of an otherwise comparable composition of matter lacking said termite attractant.

8. A method as recited in claim 7, wherein the termites are *Coptotermes formosanus*.

9. A method for killing termites, comprising the steps of placing near a termite colony a termite bait containing a termite toxicant; creating at least one trail of a termite attractant comprising 2-hydroxymethyl-7-$R^1$-8-$R^2$-naphthalene, wherein $R^1$ is methyl, ethyl, propyl, or isopropyl, and wherein $R^2$ is methyl, ethyl, propyl, or isopropyl, to lead termites to the bait; and allowing the termites to consume a sufficient amount of the bait to kill at least some of the termites in the colony.

10. A method as recited in claim 11, wherein the termites are *Coptotermes formosanus*.

11. A kit for killing termites, comprising a termite bait containing a termite toxicant; 2-naphthalenemethanol; and instructions for placing the bait near a termite colony, creating at least one trail of 2-naphthalenemethanol to lead termites to the bait, and allowing the termites to consume a sufficient amount of the bait to kill at least some of the termites in the colony.

12. A kit for killing termites, comprising a termite bait containing a termite toxicant; a termite attractant comprising 2-hydroxymethyl-7-$R^1$-8-$R^2$-naphthalene, wherein $R^1$ is methyl, ethyl, propyl, or isopropyl, and wherein $R^2$ is methyl, ethyl, propyl, or isopropyl; and instructions for placing the bait near a termite colony, creating at least one trail of the termite attractant to lead termites to the bait, and allowing the termites to consume a sufficient amount of the bait to kill at least some of the termites in the colony.

* * * * *